(12) United States Patent
Brehm (10) Patent No.: US 10,471,197 B2
(45) Date of Patent: Nov. 12, 2019

(54) CONNECTOR WITH A CONTAINER FOR PREPARING AN INDIVIDUALLY ADJUSTED SOLUTION FOR DIALYSIS

(71) Applicant: Fresenius Medical Care Deutschland GmbH, Bad Homburg (DE)

(72) Inventor: Winfried Brehm, Hofheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 87 days.

(21) Appl. No.: 14/757,785

(22) Filed: Dec. 28, 2015

(65) Prior Publication Data

US 2016/0213831 A1 Jul. 28, 2016

Related U.S. Application Data

(62) Division of application No. 13/764,316, filed on Feb. 11, 2013, now abandoned.

(60) Provisional application No. 61/597,255, filed on Feb. 10, 2012.

(30) Foreign Application Priority Data

Feb. 10, 2012 (DE) .......................... 10 2012 002 497

(51) Int. Cl.
    *A61M 1/16* (2006.01)
    *B01F 15/00* (2006.01)
    *A61J 1/20* (2006.01)

(52) U.S. Cl.
    CPC .............. *A61M 1/1668* (2014.02); *A61J 1/20* (2013.01); *A61M 1/1656* (2013.01); *B01F 15/00* (2013.01); *Y10T 137/0402* (2015.04); *Y10T 137/9029* (2015.04)

(58) Field of Classification Search
    CPC ...... A61M 1/1668; A61M 1/1656; A61J 1/20; B01F 15/00; Y10T 137/0402; Y10T 137/9029
    USPC ........................................... 141/100; 222/501
    See application file for complete search history.

(56) References Cited

U.S. PATENT DOCUMENTS

| 2,631,521 A | * | 3/1953 | Atkins, Jr. | ........... B65D 51/224 |
| | | | | 206/222 |
| 2,793,776 A | * | 5/1957 | Lipari | ................... A61J 1/2093 |
| | | | | 206/221 |
| 2,953,132 A | | 9/1960 | Richter | |
| 3,156,369 A | * | 11/1964 | Bowes | ................ B65D 51/285 |
| | | | | 206/222 |

(Continued)

FOREIGN PATENT DOCUMENTS

| DE | 3224823 | 1/1984 |
| DE | 19605260 | 11/1996 |

(Continued)

*Primary Examiner* — Timothy L Maust
*Assistant Examiner* — James R Hakomaki
(74) *Attorney, Agent, or Firm* — Jacobson Holman, PLLC.

(57) ABSTRACT

The invention relates to a connector for a container with a spiking solution for individual adjustment of dialysis solutions and/or dialysis concentrates. The connector ensures a contamination-free introduction of the spiking solution into the container of the dialysis solution and/or of the dialysis concentrate and reliable labeling of same as soon as the original contents have been altered by adding a spiking solution.

12 Claims, 6 Drawing Sheets

(56) References Cited

U.S. PATENT DOCUMENTS

| | | | | |
|---|---|---|---|---|
| 3,347,410 | A * | 10/1967 | Schwartzman | A45D 19/02 206/222 |
| 3,924,741 | A | 12/1975 | Kachur et al. | |
| 4,353,488 | A * | 10/1982 | Schneiter | B67D 3/045 222/501 |
| 4,362,158 | A * | 12/1982 | Lena | A61J 1/10 128/DIG. 24 |
| 4,705,191 | A * | 11/1987 | Itzel | B05B 11/0037 141/326 |
| 5,220,949 | A * | 6/1993 | Rufenacht | B67C 11/02 141/2 |
| 5,526,853 | A | 6/1996 | McPhee et al. | |
| 5,692,644 | A * | 12/1997 | Gueret | B05B 11/0083 206/222 |
| 5,824,216 | A * | 10/1998 | Joie | B01D 21/34 210/252 |
| 5,863,421 | A | 1/1999 | Peter, Jr. et al. | |
| 5,941,380 | A * | 8/1999 | Rothman | B65D 51/2828 206/219 |
| 6,036,858 | A | 3/2000 | Carlsson et al. | |
| 6,098,892 | A * | 8/2000 | Peoples, Jr. | G06F 19/3462 235/462.01 |
| 6,325,115 | B1 * | 12/2001 | Cowland | A01K 5/02 141/346 |
| 6,355,161 | B1 * | 3/2002 | Shah | A61M 1/1656 206/459.1 |
| 6,537,976 | B1 | 3/2003 | Gupta | |
| 6,926,138 | B1 * | 8/2005 | Basham | B65D 51/2828 206/219 |
| 7,055,685 | B1 * | 6/2006 | Patterson | B65D 51/2892 206/219 |
| 7,909,160 | B2 * | 3/2011 | Patterson | B65D 51/2892 206/221 |
| 8,025,168 | B2 * | 9/2011 | Bullard | A61J 9/008 215/11.1 |
| 8,251,110 | B2 * | 8/2012 | Bassett | A47K 5/12 141/319 |
| 8,695,819 | B1 * | 4/2014 | Anderson | B65D 51/18 206/219 |
| 9,896,258 | B2 * | 2/2018 | Lee | B65D 51/2835 |
| 2001/0040127 | A1 | 11/2001 | Donig et al. | |
| 2004/0069799 | A1 * | 4/2004 | Gee | B65D 51/227 222/83 |
| 2004/0211718 | A1 * | 10/2004 | Deguchi | A61M 1/1656 210/252 |
| 2005/0279653 | A1 * | 12/2005 | Williams-Lucas | B65D 51/285 206/219 |
| 2007/0039975 | A1 | 2/2007 | Bochtier | |
| 2007/0138183 | A1 | 6/2007 | Ritter | |
| 2011/0042944 | A1 | 2/2011 | Johns | |
| 2011/0087164 | A1 * | 4/2011 | Mosler | A61J 1/2089 604/87 |
| 2012/0123382 | A1 | 5/2012 | Kubo | |

FOREIGN PATENT DOCUMENTS

| | | |
|---|---|---|
| DE | 19814687 | 2/1999 |
| DE | 69624118 | 6/2003 |
| DE | 102005060290 | 12/2006 |
| JP | H09618 | 1/1997 |
| JP | 10085306 A * | 4/1998 |
| JP | 2001-346869 | 12/2001 |
| JP | 2001340447 A * | 12/2001 |
| JP | 2002053136 A * | 2/2002 |
| WO | WO 99/07419 | 2/1999 |

* cited by examiner

CONNECTOR WITH A CONTAINER FOR PREPARING AN INDIVIDUALLY ADJUSTED SOLUTION FOR DIALYSIS

The invention relates to a connector with a container with a so-called spiking solution for individually adjusting dialysis solutions and/or concentrates. The connector ensures a contamination-free introduction of the spiking solution into the container of the dialysis solution and/or of the dialysis concentrate and reliable identification of same as soon as the original contents have been altered by the addition of a spiking solution.

STATE OF THE ART

The individual adjustment of dialysis solutions is described in the state of the art.

In DE 32 24 823 one or more additive components is placed in a 1-liter mixing vessel and added to a canister with 9 liters of dialysis concentrate before the treatment. The dialysis solution and/or the dialysis concentrate is/are assembled in a modular fashion.

WO 99/07419 describes the addition of powdered vitamins and trace elements from commercial vials to liquid bicarbonate concentrate.

Statement of Problem

Solutions for hemodialysis are often prepared from concentrates, which are diluted with ultrapure water by the dialysis machine online, in particular in the treatment of chronic renal failure. The concentrates containing the required electrolytes are prepared by the care personnel in bags or canisters on the dialysis machine. Then the dialysis machine has a tapping means, for example, in the form of an intake rod by means of which the concentrate is pumped into the machine and diluted with water there, preferably from a central supply unit.

With the typical bicarbonate dialysis today, two concentrates are usually required, namely one basic concentrate, which contains the bicarbonate buffer and optionally sodium chloride, and an acidic concentrate, which contains additional electrolytes, e.g., magnesium, calcium, potassium, glucose and an acid in addition to sodium chloride. The basic concentrate is usually supplied as a dry concentrate and consists only of sodium bicarbonate or sodium bicarbonate combined with sodium chloride. The acidic concentrate is usually a liquid concentrate, which is supplied in plastic canisters with a volume of 3-10 liters each. The liquid concentrates have a composition, such that an electrolyte solution corresponding largely to the composition of physiological, i.e., healthy, blood plasma is obtained after dilution. These liquid concentrates are offered in only a few standard compositions.

Renal failure may be caused by a variety of diseases. Dialysis treatment itself still constitutes a serious intervention into the human body and may cause various complications and comorbidities. The initial situation at the start of treatment may therefore vary from one patient to the next. Very high potassium concentrations are found in many patients before dialysis. To make dialysis gentler, the potassium concentration in the dialysate may also be selected to be somewhat higher here. The same thing is also conceivable for the other electrolytes. Whereas an excessively high phosphate burden is found with most dialysis patients, many patients who have undergone very extensive dialysis may suffer from hypophosphatemia, which can be treated by adding phosphate to the dialysis solution. Malnutrition is another challenge often confronting dialysis patients. An improvement can be achieved here by adding glucose, vitamins or amino acids to the concentrate. In addition, the unintentional removal of trace elements from blood can be counteracted by the dialysis treatment as needed by replenishing these trace elements in the dialysis solution. The individual requirements of the precise composition of the dialysis solution used thus cover a large spectrum and the individual adjustment of the dialysis solution to the respective needs of the patient can minimize adverse effects and improve the success of treatment.

On the other hand, there is limited storage capacity in the clinic, so that only a limited number of different dialysis concentrates can be kept on hand. At the same time, production and storage of a great many different concentrates would require extensive logistics.

The additional components may be added to the standard concentrates as high-concentration solutions, so-called spiking solutions, or as powders. The altered composition must then be noted by hand on the canister by the nurse/caregiver, so that this will be unambiguously identifiable for a third party when the canister is used for multiple treatments, for example. There is the risk here that the notation may be forgotten and/or that the inscription is discernible from only one side or is also easy to overlook. In addition, transferring liquids from one vessel to another vessel without any transfer systems is burdened with a risk of contamination or the risk that some of the solution may be spilled.

The object of the present invention is to provide a system and a method which will ensure reliable transfer of an additional component, e.g., in the form of a spiking solution, to a standard dialysis concentrate and reliable identification of same.

According to the teaching of the invention, this object is achieved by a connector according to the features of claim 1, a combination of the connector with a second container according to claim 11 and a method for preparing and identifying an individually adjusted solution for dialysis according to claim 12. Advantageous embodiments are the basis of the dependent claims.

SUMMARY OF THE INVENTION

The invention relates to a connector with a first container for a substance for individual adjustment of a solution for dialysis. The connector has at least one opening, which is closed by a closure means. The connector is suitable for attachment to a second container. After being connected to the second container, a fluid connection between the first and second containers can be established by opening the closure means through which the substance for individually adjusting the solution for dialysis can flow from the first container into the second container. After connecting the connector to the second container, at least the connector remains on the second container and identifies it.

The connector and the first container may be designed in one piece. The connector and container may be designed, so that they can be attached to the opening of the second container. However, they may also have a thread with which they can be screwed onto the second container. The first container may in this case be in the shape of a double-walled funnel, for example, which is filled with the substance and is attached to a canister, for example. The double wall of plastic is open at the bottom and is closed before use by a closure means, e.g., a welded film, which extends over the entire circular cutout of the bottom part of the funnel. For use of the solution for dialysis in the second container, the tapping means of the dialysis device is then inserted through an opening into the connector and to the second container, the concentrate canister. In doing so, the closure means is released from the bottom side of the first container, so that the substance enters the canister. The closure means is welded to the bottom side, so that it is first released from the inner ring and thus establishes a fluid connection between the first and second containers. Then it is also released from the outside edge, but only partially, so that the closure means remains on the connector and does not fall into the concentrate container.

The connector is definitely identified by an inscription which indicates the type of spiking solution, i.e., the contents of the first container. At least the connector or, in an alternative embodiment, also the connector together with the first container remains on the second container during use and thereby identifies the modified composition of the contents of the second container, i.e., the concentrate container.

The connector and the first container may consist of two parts each. The first container with the spiking solution may then be designed so that, in a first state, it closes the opening of the connector, so that it forms the closure means. In a first step, the connector with the first container is placed on the concentrate container or screwed onto it. Then openings, e.g., cutouts in the container wall are exposed by a displacement of the container, and a fluid connection is established between the first and second containers. The substance can flow from the first container into the second container and thus adjust the composition to the individual needs of the patient. For introducing the tapping means of the dialysis machine into the concentrate container, the first container must be removed to form an opening for insertion of the tapping means. The connector remains on the concentrate container. The connector and the contents of the first container are identified in this case. The connector remains on the concentrate container during its entire use and identifies it.

In another embodiment according to the invention, the connector has two openings. A first opening serves as access for the tapping means of the dialysis machine to the concentrate container. This first opening is largely circular and is arranged centrally in the connector. The diameter is selected so that simple access to the concentrate container is possible.

A second opening may serve to establish the fluid connection between the first and second containers. The first container with the spiking solution is then inserted into this second opening. The second opening is preferably arranged on the inside edge of the first opening.

The closure means is preferably formed by a welded film, which seals both openings. It may extend over the entire lower surface of the connector.

In a first step, the connector with the first container is attached to or screwed onto the concentrate container. If the tapping means of the dialysis machine leads through the opening provided for this purpose, the closure means is released, forming a passage for the tapping means and at the same time establishing a fluid connection between the first and the second container. This is ensured by the type of welding of the film. The film is welded less strongly to the opening to the first container than to the outside edge of the second opening. The welded connection at the first opening is therefore released first, and then the welded connection at the outside edge of the second opening is released. The welded connection at the outside edge of the second opening is preferably only partially releasable, so that after opening the connection, the closure means remain on the connector and do not enter the concentrate container. Contact between the solution for dialysis and the closure means is therefore prevented, thus reducing the risk of contamination.

The connector and the first container may be provided with an outer packaging, which also contributes to a reduction in the risk of contamination. The outer packaging may consist of a bag surrounding the connector and the first container. However, the outer packaging may also be designed as a cover, which covers only the lower base area of the connector that comes in contact with the concentrate container during use.

The substance in the first container for individual adjustment of a solution for dialysis is either present as a highly concentrated solution (spiking solution) or as a powder. Substances that can be used for individual adjustment of a solution for dialysis include, for example, electrolytes such as KCl, $CaCl_2$, $MgCl_2$, etc., vitamins, trace elements, phosphate, iron or glucose. The first container preferably has a definitely smaller volume than the second container. The volume of the first container may be between 10 and 300 mL. The second container holds the solution for dialysis. This solution may be a ready-to-use solution for dialysis. It is preferably a concentrate, which is diluted online with water or a solution of other ingredients for dialysis by a dialysis machine. It is especially preferably the acidic concentrate of bicarbonate dialysis. The second container, preferably the concentrate container, is preferably a canister or a bag with a volume of 3-12 liters.

The invention also relates to a combination of a connector with a first container and a second container as described above. The first container may contain a substance for individual adjustment of a solution for dialysis contained in the second container, preferably a dialysis concentrate. Complete contamination-free transfer of the contents of the first container to the second container is made possible by the connector. This combination provides an obvious identification of the second container which helps to prevent mistakes in use.

The invention also relates to a method for producing and identifying an individually adjusted solution for dialysis by connecting a first container and a second container using a connector as described above. Opening the closure means results at least in a fluid connection between the first and second containers. After producing the fluid connection, there remains at least the connector on the second container, which provides the identification of the second container.

The closure means may be formed by the first container itself, in which case the fluid connection can be established by shifting the first container.

The closure means may preferably be formed by a welded film, which is preferably released partially from the connector by inserting the tapping means of the dialysis machine, so that the opening of the fluid connection between the first container and the second container is ensured due to differences in the strength of the weld.

Additional details and advantages of the invention will now be described in greater detail on the basis of the exemplary embodiments depicted in the drawings, which show.

DESCRIPTION OF THE EXEMPLARY EMBODIMENTS

Figure 1:
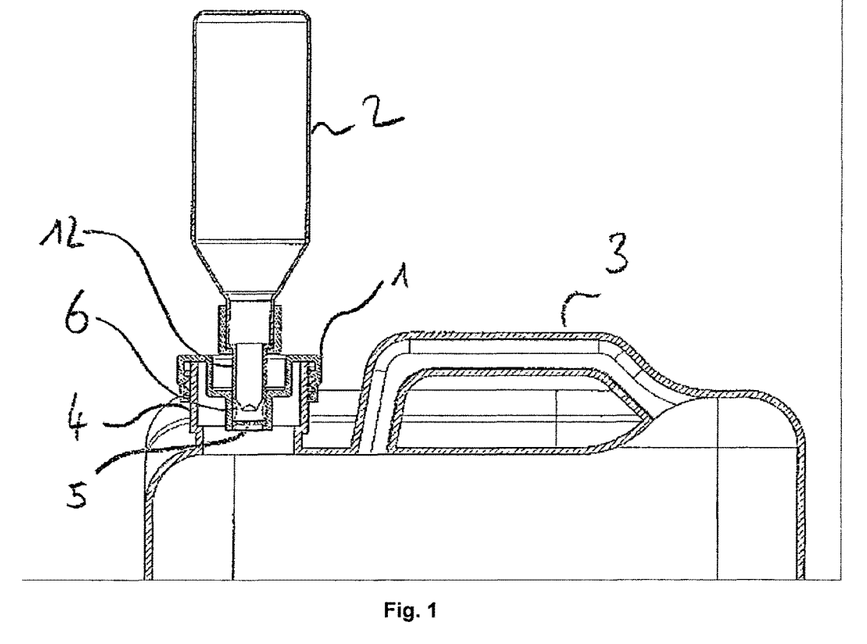
FIG. 1: Cross section through a first embodiment of a connector according to the invention with a first container in the closed state screwed onto the concentrate canister.

FIG. 1 shows the cross section through a first connector 1 with a first container 2. The connector 1 is screwed onto a canister 3 with acidic concentrate. The container 2 contains the spiking solution.

In the embodiment shown here, the container 2 consists of a vessel which is inserted into the connector 1 by means of a bulb-shaped protrusion 12. The bulb-shaped protrusion 12 has a closed face 5 at the head end, while two cutouts 6 are provided at the sides. In a first position, the face 5 is flush with the lower edge of the opening of the connector 1, the cutouts 6 at the sides being sealed by the connector 1. In this configuration, the container is sealed tightly, so there is no fluid connection between the container 2 and the canister 3 with the acidic concentrate.

Figure 2:
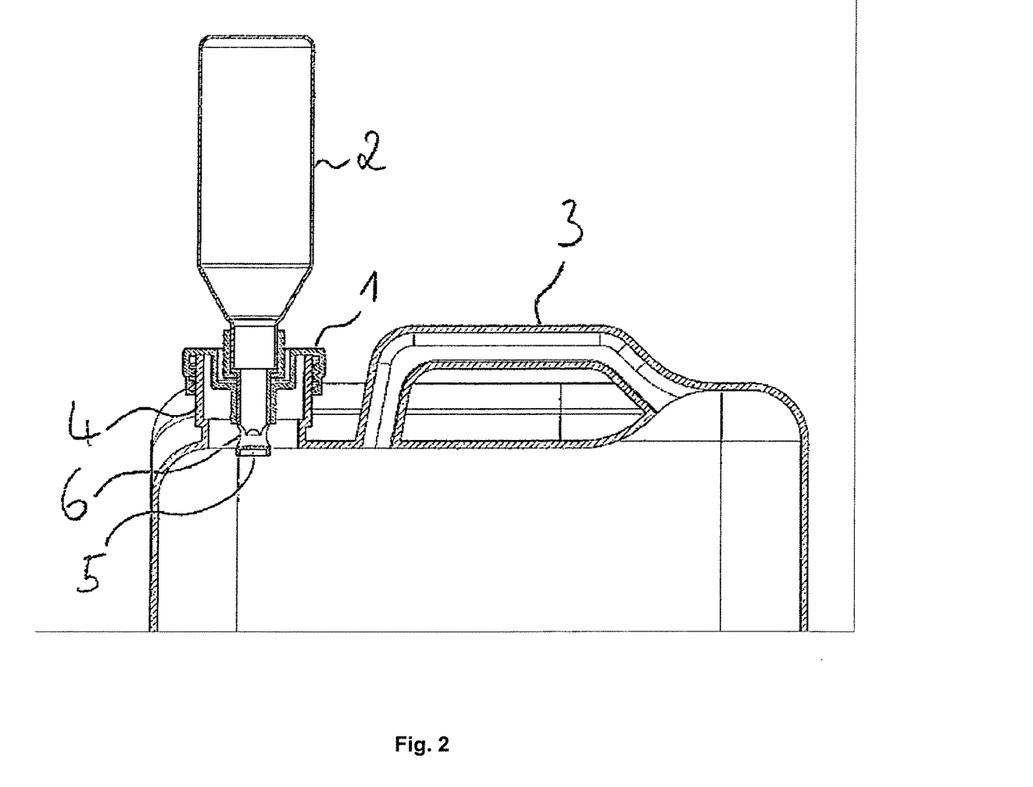
FIG. 2: Cross section through the connector shown in FIG. 1 with the first container in an opened state screwed onto a concentrate canister.

To establish such a fluid connection, the first container 2 is displaced downward in the connector 1, as shown in FIG. 2, so that the part of the bulb-shaped protrusion with the cutouts 6 at the side protrudes into the canister 3. Then the contents of the container 2 can flow into the acidic concentrate through the cutouts 6 at the side without running the risk that part of the solution will be spilled or contaminated. After the container 2 has been emptied, it is withdrawn from the connector 1. The tapping means of the dialysis machine, e.g., a concentrate suction rod, can be inserted through the central opening in the connector 1 into the canister 3, and concentrate can be transferred to the dialysis machine while the connector 1 remains on the canister 3. The connector 1 has an inscription, which describes the contents of the container. The user can thus recognize at first glance that the contents of the canister no longer conform to the standard composition.

Figure 3:
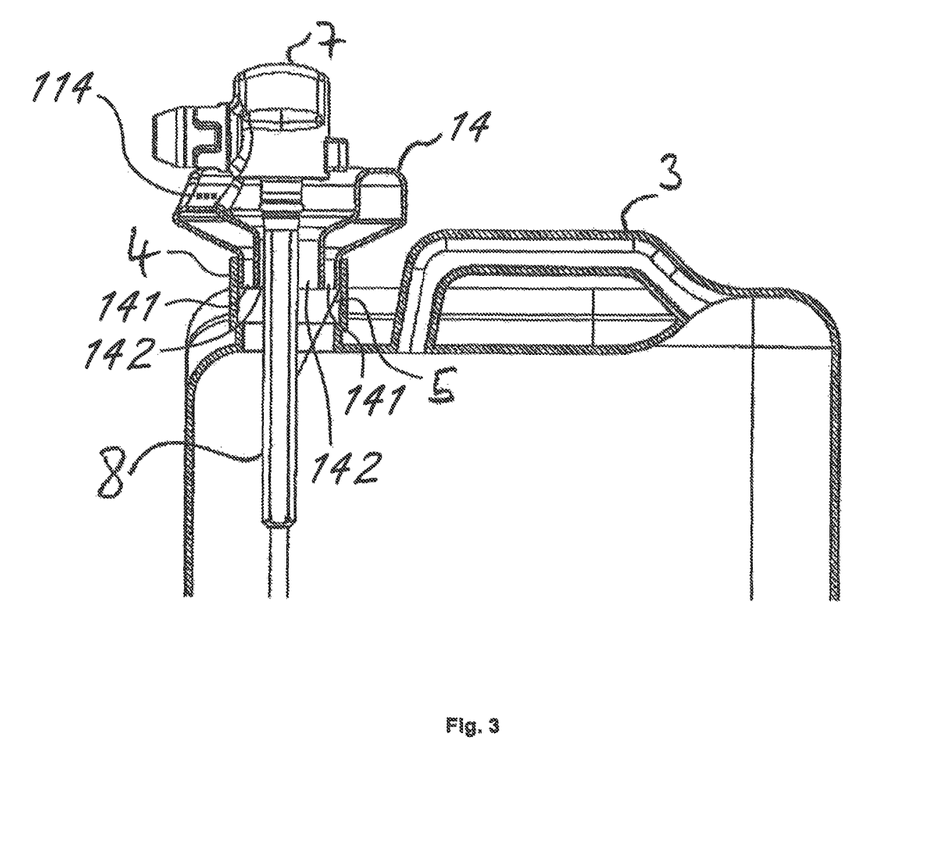
FIG. 3: Cross section through a second embodiment of a connector according to the invention, embodied in one piece with the first container, attached to a concentrate canister with the concentrate intake rod inserted.

FIG. 3 shows a second embodiment in which the connector and the container 14 are embodied in one piece. In the embodiment shown here, the device is in the form of a double-walled funnel, which is inserted into the opening in the canister 3. A closure means 5 in the form of a welded film is applied to the underside of the funnel, closing both the central second opening 142 in the funnel and the ring-shaped first opening 141 in the container 14. The central opening in the funnel is used as access for the tapping means 7 of the dialysis machine with the concentrate suction rod 8. The container 14 remains on the canister 3 during use of the latter. If the concentrate suction rod is inserted into the canister through the central opening, the closure means is released from the container 14. Due to the difference in weld strengths, the film is released first at the inner ring of the outlet of the double-walled funnel. Then the film is partially released on the outer ring. The film is welded to the outer ring in such a way that there is no complete separation. The closure means 5 remains on the container 14, while the fluid connection between the container 14 and the container 3 is established. The container 14 has a definite inscription 114, which describes the contents of the container. It is thus possible for the user to recognize at first glance that the contents of the canister no longer conform to the standard composition.

Figure 4:
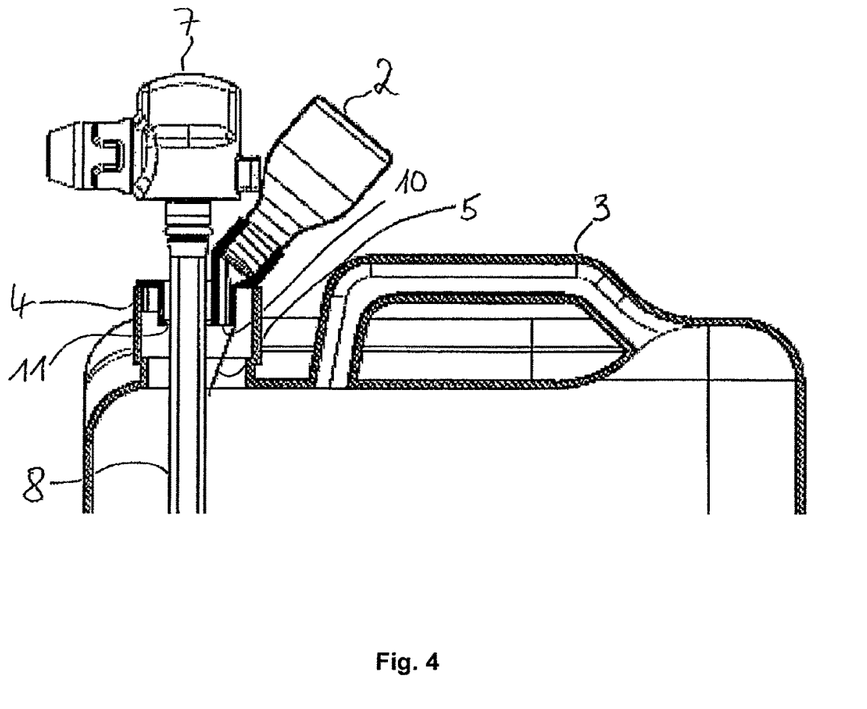
FIG. 4: Cross section through a third embodiment of a connector according to the invention with a first container attached to a concentrate canister and the concentrate intake rod inserted.

FIG. 4 shows a third embodiment of the invention in which the connector 1 and container 2 are embodied in two parts. In this embodiment at the least the connector 1 remains on the canister opening 4 during the use of the canister 3. It is likewise possible to leave the connector 1 and container 2 on the canister 3. The inscription can then be applied to the connector 1 or to the container 2.

The connector 1 is attached here to the canister opening 4. It has a large central opening 11 through which the concentrate intake rod 8 is introduced into the canister 3. In addition to this central opening, the connector 1 has an additional opening 10. This opening 10 forms the outlet of a fluid line through the connector 1 on the canister end. At the outlet of the fluid line on the room end, the container 2 is screwed into the connector 1. Before inserting the intake rod 8, the two openings are both sealed by the connector means 5 in the form of a welded film.

If the concentrate intake rod 8 is introduced into the canister 3 through the central opening 11, the closure means 5 is released by the connector 1. Due to different weld strengths, the release of the film takes place first at the opening 10 of the fluid line to the container 2. Then the film is partially separated on the outer ring of the central opening 11. The film is welded there in such a way that there is no complete separation. The closure means 5 remains on the connector 1, while the fluid connection between the container 2 and container 3 is established. Since the connector 1 is attached tightly to the canister 3, there is no risk that some of the contents will be spilled during transfer of the spiking solution to the concentrate canister 3.

Figure 5:
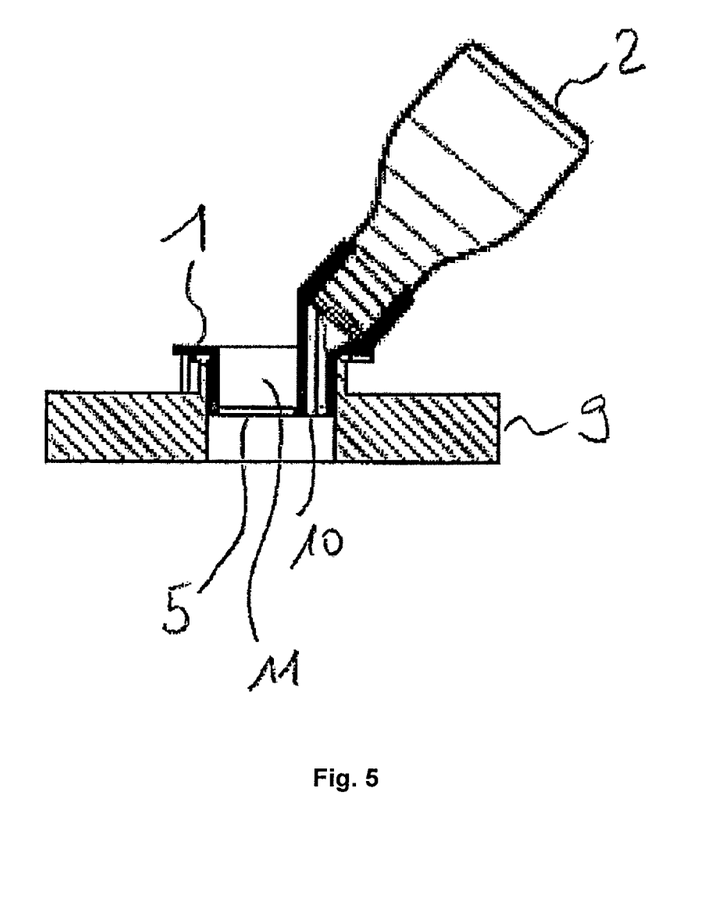
FIG. 5: Cross section through the third embodiment of a connector according to the invention with the first container attached to an insert piece for a concentrate bag.

FIG. 5 shows the connector 1 according to FIG. 4. It is not attached to a concentrate canister here but instead is inserted into an insertion piece 9 such as that used with concentrate bags. The device is shown before insertion of the concentrate suction rod. The closure means 5 still closes the central opening 11 and the opening 10 of the fluid connection to container 2.

Figure 6:
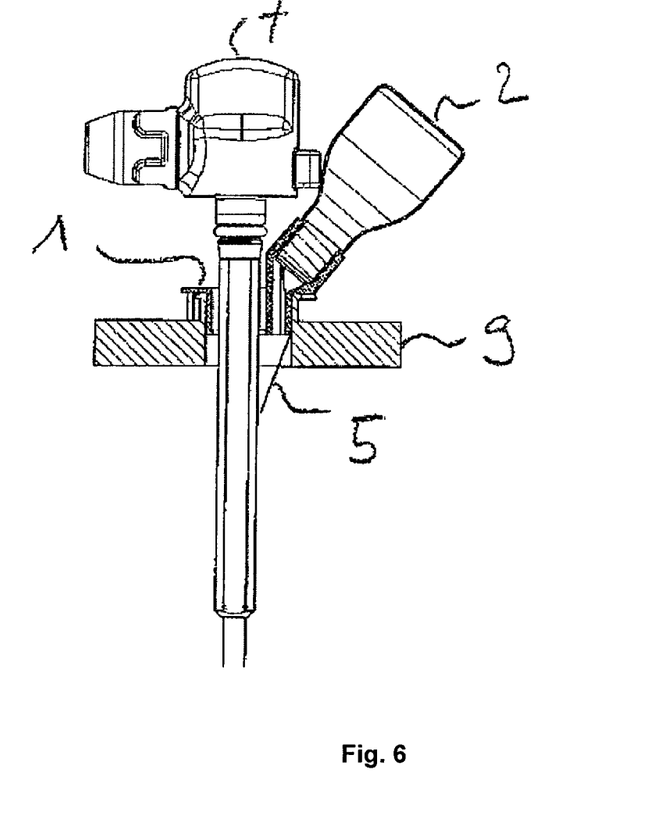
FIG. 6: Cross section through the third embodiment of the connector according to the invention with the first container attached to the insert piece for a concentrate bag and with the concentrate intake rod inserted.

FIG. 6 shows the device according to FIG. 5 after insertion of the concentrate suction rod 8.

The present invention ensures reliable transfer of a spiking solution to the concentrate container. The change in the composition of the standard concentrate is easy for the user to recognize due to the connector remaining on the concentrate container.

The invention claimed is:
1. A combination comprising
   a) a first container for holding a spiking solution for individual adjustment of a dialysis solution and
   b) a connector configured for attachment to a second container, having an inscription identifying the spiking solution, and having an axial orientation, a ring shaped first opening in fluid communication with the first container, an axially aligned second opening configured for axially inserting a tap, a closure closing the first and second openings and configured to be opened by axially inserting the tap through the second opening, wherein the combination is configured such that after removably attaching the connector to a second container by vertically inserting the tap in the second opening the closure is opened forming a fluid connection between the first and second containers.

2. The combination of claim 1 wherein the first container and the connector are designed in one piece.

3. The combination of claim 1 wherein the closure is a film welded to the connector.

4. The combination of claim 1 further comprising the axially inserted tap configured for removing contents from the second container via the connector.

5. The combination of claim 1 wherein the closure is further configured to maintain contact with the connector after the closure is opened.

6. The combination of claim 1 wherein the spiking solution contains at least one water-soluble substance selected from the group consisting of an electrolyte, a nutrient, a vitamin, and a trace element formulated for the individual adjustment of a dialysis solution.

7. A system comprising the combination of claim 1 and a second container removably attached to the connector.

8. The system of claim 7 wherein the second container holds an acidic concentrate for bicarbonate analysis and the spiking solution is for individual adjustment of the acidic concentrate.

9. A system comprising the combination of claim 4 and a second container removably attached to the connector.

10. The system of claim 9 wherein the second container holds an acidic concentrate for bicarbonate analysis and the spiking solution is for individual adjustment of the acidic concentrate.

11. A method for producing and identifying an individually adjusted solution for dialysis comprising removably attaching the combination of claim 1 to a second container and axially inserting the tap in the second opening and thereby the closure is opened forming a fluid connection between the first and second containers, wherein the second container holds a dialysis solution or concentrate and the spiking solution is for the individual adjustment of the dialysis solution or concentrate.

12. The method of claim 11 wherein the closure maintains contact with the connector after the closure is opened.

* * * * *